united States Patent [19]
Chang et al.

[11] Patent Number: 4,920,106
[45] Date of Patent: Apr. 24, 1990

[54] ACETYLENIC CYCLIC CARBONATES

[75] Inventors: Michael N. Chang, Westfield; Yuan-Ching P. Chiang, Piscataway; James V. Heck, Scotch Plains; Michael D. Lewis, Rahway; Shu S. Yang, Bridgewater, all of N.J.

[73] Assignee: Merck & Co., Inc., Rahway, N.J.

[21] Appl. No.: 388,716

[22] Filed: Aug. 1, 1989

Related U.S. Application Data

[63] Continuation of Ser. No. 156,111, Feb. 16, 1988, abandoned.

[51] Int. Cl.$^5$ .................. A61K 31/695; C07D 317/20
[52] U.S. Cl. ...................................... 514/63; 514/467; 549/214; 549/229; 549/215

[56] References Cited

U.S. PATENT DOCUMENTS

| | | | |
|---|---|---|---|
| 4,118,540 | 10/1978 | Amort et al. | 549/214 |
| 4,332,729 | 6/1982 | Renga et al. | 549/229 |
| 4,423,235 | 12/1983 | Burgard et al. | 549/229 |
| 4,602,006 | 7/1986 | Krantz et al. | 549/214 |
| 4,780,311 | 10/1988 | Onishi et al. | 514/467 |
| 4,806,565 | 2/1989 | Hensens et al. | 549/229 |
| 4,806,566 | 2/1989 | Zimmerman | 514/467 |

OTHER PUBLICATIONS

J. Patel et al., Novel Antifungal Antibiotics, Sch 31828, produced by Microbispora sp. SCC 1438, Abst. 983 of the 1987 Interscience Conference on Antimicrobial Agents & Chemotherapy.

M. D. Lewis & R. Menes, "Absolute and Relative Configuration of L-660,631," Tetrahedron Lett., 43, 5129-5132 (1987).

R. M. Hanson & K. B. Sharpless, "Procedure for the Catalytic Asymmetric Epoxidation of Allylic Alcohols in the Presence of Molecular Sieves," J. Org. Chem., 51, 1922-1925 (1986).

M. Mehrabian et al., "Regulation of Rat Liver 3-Hydroxy-3-Methylglutaryl Coenzyme A Synthetase ...," J. Biol. Chem., 261, 16249-16255 (1986).

Primary Examiner—Richard L. Raymond
Attorney, Agent, or Firm—Richard S. Parr; Michael S. Sudol

[57] ABSTRACT

This invention relates to acetylenic cyclic carbonates that are useful in the treatment of fungal diseases and hypercholesterolemic conditions.

23 Claims, No Drawings

ACETYLENIC CYCLIC CARBONATES

This is a continuation, of application Ser. No. 156,111, filed February 16, 1988 now abandoned.

BACKGROUND OF THE INVENTION

This invention relates to acetylenic cyclic carbonates that are useful in the treatment of fungal diseases and hypercholesterolemic conditions.

Fermentation broths of certain strains of *Streptoverticillium hiroshimense* and *Nocardia* have been shown to produce the triyne carbonate 5-(1-hydroxy-2,4,6-heptatriynyl)-2-oxo-1,3-dioxolane-4-heptanoic acid, Formula A,

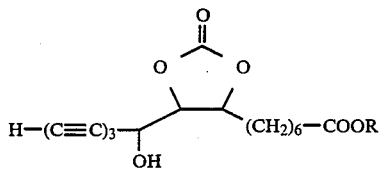

A wherein R is hydrogen, or salts thereof, M. D. Lewis and R. Menes, *Tetrahedron Lett.*, 28, 5129–5132 (1987); see also U.S. patent application Ser. Nos. 07/053,920 (now U.S. Pat. No. 4,806,565), 07/053,921, (now U.S. Pat. No. 4,806,566), 07/053,926, and 07/053,973 (now U.S. Pat. No. 4,780,311), all filed May 26, 1987. The triyne carbonate A is a potent inhibitor of cytosolic β-ketothiolase, the initial enzyme of cholesterol biosynthesis, and is also active against certain fungal and bacterial strains. Utility against hypercholesterolemia and infectious diseases is limited, however, by the relative instability of the compound in vivo. The compounds of the present invention have been prepared as part of a program to improve both inherent biological activity and in vivo stability relative to the triyne carbonate of Formula A.

SUMMARY OF THE INVENTION

Applicants have discovered novel acetylenic cyclic carbonates of Formula I that are useful in the treatment of fungal diseases and hypercholesterolemic conditions.

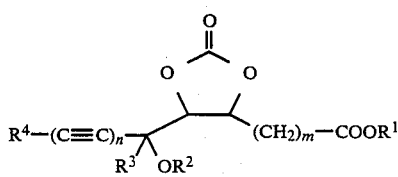

I wherein
$R^1$ is:
  (a) hydrogen;
  (b) $C_1$–$C_6$ alkyl;
  (c) $C_7$–$C_{14}$ aralkyl;
  (d) tris($C_1$–$C_6$ alkyl)silyl; or
  (e) a pharmaceutically acceptable cation;
$R^2$ is:
  (a) hydrogen;
  (b) $C_1$–$C_6$ alkyl;
  (c) $C_7$–$C_{14}$ aralkyl;
  (d) tris($C_1$–$C_6$ alkyl)silyl;
  (e) $C_2$–$C_6$ alkanoyl;
  (f) $C_2$–$C_7$ alkoxycarbonyl; or
  (g)

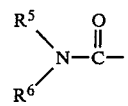

wherein $R^5$ and $R^6$ are independently:
  (i) hydrogen;
  (ii) $C_1$–$C_6$ alkyl; or
  (iii) phenyl;
$R^3$ is:
  (a) hydrogen; or
  (b) $C_1$–$C_6$ alkyl; or $R^2$ and $R^3$ taken together are a bond;
$R^4$ is:
  (a) $C_1$–$C_6$ alkyl;
  (b) $C_7$–$C_{14}$ aralkyl; or
  (c) tris($C_1$–$C_6$ alkyl)silyl;
m is an integer of from about 2 to 8; and
n is an integer of from about 1 to 4.

The term "$C_1$–$C_6$ alkyl" refers to straight or branched chain aliphatic hydrocarbons having from 1 to 6 carbon atoms and is also referred to as lower alkyl. Examples of $C_1$–$C_6$ alkyl are methyl, ethyl, propyl, butyl, pentyl, hexyl, and the isomeric forms thereof.

The term "$C_7$–$C_{14}$ aralkyl" refers to straight or branched chain alkyl groups bearing a phenyl or naphthyl group such that the total number of carbon atoms ranges from 7 to 14. Examples of $C_7$–$C_{14}$ aralkyl are benzyl, phenethyl, phenylpropyl, (1-naphthyl)methyl, (2-naphthyl)methyl, (1-naphthyl)ethyl, (2-naphthyl)ethyl, and the like, and isomeric forms thereof.

The term "tris($C_1$–$C_6$ alkyl)silyl" refers to a trisubstituted silyl group in which the $C_1$–$C_6$ alkyl groups may be the same or different. Examples of tris($C_1$–$C_6$ alkyl)silyl are trimethylsilyl, triethylsilyl, tert-butyldimethylsilyl, and the like.

The term "$C_2$–$C_6$ alkanoyl" refers to straight or branched chain alkanoyl groups having from 2 to 6 carbon atoms. Examples of $C_2$–$C_6$ alkyl are acetyl, propanoyl, butanoyl, pentanoyl, hexanoyl, and the isomeric forms thereof.

The term "$C_2$–$C_7$ alkoxycarbonyl" refers to straight or branched chain alkoxycarbonyl groups having from 2 to 7 carbon atoms. Examples of $C_2$–$C_7$ alkoxycarbonyl are methoxycarbonyl, ethoxycarbonyl, propoxycarbonyl, butoxycarbonyl, pentyloxycarbonyl, hexyloxycarbonyl, and the isomeric forms thereof.

The term "pharmaceutically acceptable cation" refers to a positively charged inorganic or organic ion that is generally considered suitable for human consumption. Examples of pharmaceutically acceptable cations are hydrogen, alkali metal (lithium, sodium, and potassium), magnesium ($\frac{1}{2}$ Mg$^{++}$), calcium ($\frac{1}{2}$ Ca$^{++}$), aluminum ($\frac{1}{3}$ Al$^{+++}$), titanium ($\frac{1}{4}$ Ti$^{++}$), zinc ($\frac{1}{2}$ Zn$^{++}$), ammonium, alkylammonium, dialkylammonium, trialkylammonium, tetraalkylammonium, diethanolaminium, triethanolaminium, and guanidinium ions, and protonated forms of lysine, benzathine, procaine, chloroprocaine, choline, and meglumine. Cations may be exchanged by methods known in the art, such as ion exchange. Where compounds of Formula I are prepared in the carboxylic form, addition of a base form of the cation (such as a hydroxide or a free amine) will yield the appropriate cationic form.

Compounds of Formula I in which $R^2$ and $R^3$ are taken together to form a bond are ketones. That is, the moiety $C(OR^2)(R^3)$ represents a carbonyl function, C=O.

It is to be recognized that certain compounds of Formula I possess one or more asymmetric carbon atoms and that certain compounds of this invention can exist as two or more optical isomers. Since these isomers may possess markedly different biological properties, it is advantageous to separate the enantiomers and use them in their pure form. The optically pure compounds of Formula I can be prepared from optically pure precursors. Alternatively, the compounds of Formula I can be resolved to their pure enantiomers by one or more methods known in the art. For example, compounds of Formula I in which $R^1$ is hydrogen or a corresponding pharmaceutically acceptable cation may be resolved by forming in a suitable solvent a salt of the racemic mixture with an optically active base such as (+)— or (−)-amphetamine, brucine, (+)-cinchonine, (−)-cinchonidine, strychine, (+)— or (−)-alpha-methylbenzylamine, (+)— or (−)-alpha-(1-naphthyl)ethylamine, and the like. Examples of suitable solvents include ethanol, isopropyl alcohol, benzene, acetonitrile, nitromethane, acetone, and the like. Two diasteromeric salts form in the solution, one salt usually being less soluble than the other. Repetitive recrystallization of the crystalline salt generally affords a pure diastereomeric salt from which is obtained the desired pure enantiomer, for example, by acidification of the salt with a mineral acid, filtration, and recrystallization.

The other optically pure antipode may generally be obtained by using a different optically active base to form the diastereomeric salt. It may be advantageous to isolate the partially resolved acid from the filtrates of the purification of the first diastereomeric salt, described above, and to purify further this substance through the use of another optically active base. It is especially advantageous for isolating the second enantiomer to use an optically active base that is the antipode of the base used for isolating the first enantiomer. For example, if (+)-alpha-methylbenzylamine was used first, then (−)-alpha-methylbenzylamine would be used to isolate the second (remaining) enantiomer.

DESCRIPTION OF THE INVENTION

The compounds of this invention can be prepared by methods illustrated in the following Schemes. Scheme A illustrates one method for preparing cyclic carbonate intermediates of Formula VI.

SCHEME A

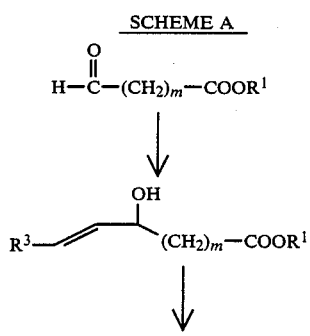

-continued
SCHEME A

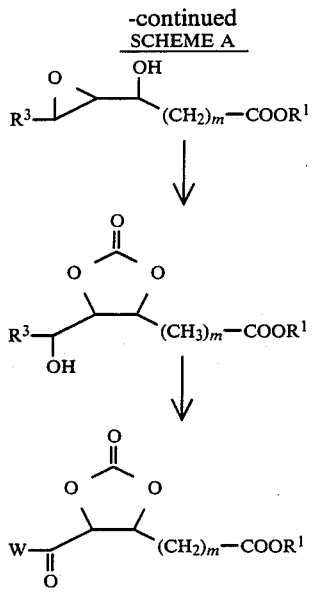

Aldehyde esters of Formula II can be converted to allylic alcohols of Formula III by any of several methods known in the art. A preferred method employs a Grignard reaction. For example, reaction of aldehyde II with a vinyl magnesium bromide (having the formula $R^3$—CH=CH—MgBr) in a suitable organic solvent (preferably tetrahydrofuran) at reduced temperatures (preferably about −78° C.) affords the allylic alcohol III in good yields. Other suitable organic solvents for the reaction are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art.

Allylic alcohols of Formula III are epoxidized by methods known in the art to form corresponding epoxy alcohols of Formula IV. A preferred epoxidation method employs a titanium (IV) salt (preferably titanium tetraisopropoxide) and an alkyl hydroperoxide (preferably t-butyl hydroperoxide) in a suitable solvent and is best performed in the presence of 3A molecular sieves. Suitable organic solvents for epoxidation are organic liquids in which the various reactants can be dissolved or suspended but which are otherwise chemically inert. Examples of suitable organic solvents include alkanes and cycloalkanes; aromatic hydrocarbons, such as benzene, toluene, and xylene; halocarbons, such as chloroform, dichloromethane, and ethylene dichloride; and other organic solvents known in the art. A preferred organic solvent is dichloromethane. Optically active epoxy alcohols of Formula IV can be prepared by the inclusion of an optically active induction agent such as L-(+)-diisopropyl tartrate (L-(+)-DIPT) or other such tartrate esters. For example, R. M. Hanson and K. B. Sharpless, J. Org. Chem., 51, 1922–1925 (1986).

The alcohol function of a compound of Formula IV is first acylated with a carbamate forming reagent using methods known in the art, and the resultant acylated intermediate is then ring closed to form the cyclic carbonate of Formula V. Acylation is preferably performed using an aromatic isocyanate, preferably phenyl isocyanate, in a suitable organic solvent. An alternative acylation method uses a carbamoyl halide in a suitable organic solvent containing a suitable amine base. Suitable organic solvents for acylation are organic liquids in which the various reactants can be dissolved or suspended but which are otherwise chemically inert. Examples of suitable organic solvents include alkanes and cycloalkanes; alkanoate esters, such as ethyl acetate; ethers and cyclic ethers, such as diethyl ether, tetrahydrofuran, tetrahydropyran, and dioxane; aromatic hydrocarbons, such as dimethylformamide and N,N-dimethylacetamide; N-substituted lactams, such as N-methylpyrrolidinone and N-methylpiperidinone; halocarbons, such as chloroform, dichloromethane, and ethylene dichloride; cyanoalkanes, such as acetonitrile and propanenitrile; and other organic solvents known in the art. A preferred organic solvent is acetonitrile. Suitable amine bases are organic compounds that facilitate acylation and are sufficiently basic to prevent the reaction medium from becoming acidic but which do not themselves form significant quantities of by-products by reaction with other chemical reagents, intermediates, or reaction products. Suitable amine bases include tertiary amines and nitrogen-containing heteroaromatic compounds. Suitable tertiary amines include trialkylamines, such as triethylamine and tributylamine; N-substituted saturated heterocyclic compounds, such as N-methylmorpholine, N-methylpiperidine, and N,N-dimethylpiperazine; polybasic tertiary amines, such as N,N,N,N-tetramethylethylenediamine and N,N,N,N-tetramethylpropylenediamine; and other tertiary amines known in the art. Suitable nitrogen-containing heteroaromatic compounds include 1-methylpyrrole, pyridine, lutidine, pyrazine, pyrimidine, pyridazine, quinoline, isoquinoline, 1-methylimidazole, 1-methylpyrazole, dimethylaminopyridine, and other such nitrogen-containing heteroaromatic compounds known in the art. A preferred amine base is pyridine.

Ring closure of the acylated intermediate to compounds of Formula V can be effected by any of several methods known in the art. A preferred ring closure method involves a Lewis-acid catalyzed reaction in a suitable organic solvent at reduced temperatures, preferably below at least about $-20°$ C. A preferred Lewis acid is boron trifluoride etherate. Suitable organic solvents for Lewis-acid catalyzed ring closure are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is diethyl ether.

The alcohol group of a cyclic carbonate of Formula V is then modified to form compounds of Formula VI in which W is $R^3$ (that is, aldehydes or ketones; see Scheme B, below) or a leaving group L (that is, activated acyl compounds; see Scheme C, below) for subsequent reactions. Conversion of compounds V to aldehydes or ketones of Formula VI in which W is $R^3$ can be effected using any of several oxidation methods known in the art. For example, a preferred oxidation method employs a mixture of oxalyl chloride and dimethyl sulfoxide at reduced temperatures (preferably below at least $-35°$ C.) in a suitable organic solvent that is essentially inert under oxidative conditions, preferably tetrahydrofuran.

Conversion of compounds V to activated acyl compounds of Formula VI in which W is a leaving group L can be effected using methods known in the art. An alcohol of Formula V is first oxidized to the corresponding carboxylic acid (that is, where W is OH) by any of several methods known in the art, and the resultant carboxylic acid is then converted to the desired activated acyl compound. A preferred method of oxidations uses Cr(VI) or permanganate under a variety of reaction conditions. For example, compounds of Formula V can be oxidized in high yields using Jones oxidation with chromium trioxide in a mixture of sulfuric acid and acetone. Where the desired leaving group L is a halogen, preferably chlorine or bromine, the activated acyl compound of Formula VI is an acid halide. Acid halides can be formed by a wide variety of methods using such reagents as oxalyl chloride, phosgene, phosphorus oxyhalides, thionyl halides, an the like. A preferred method for preparing acyl chlorides uses oxalyl chloride in a suitable organic solvent. Suitable organic solvents for preparing acyl halides are organic liquids in which the various reactants can be dissolved or suspended but which are otherwise chemically inert. Examples of suitable organic solvents for preparing acyl halides using oxalyl chloride include alkanes and cycloalkanes; alkanoate esters, such as ethyl acetate; ethers and cyclic ethers, such as diethyl ether, tetrahydrofuran, tetrahydropyran, and dioxane; aromatic hydrocarbons, such as benzene, toluene, and xylene; halocarbons, such as chloroform, dichloromethane, and ethylene dichloride; cyanoalkanes, such as acetonitrile and propanenitrile; and other organic solvents known in the art. A preferred organic solvent is dichloromethane.

Where the desired leaving group L is O-acyl, the activated acyl compound of Formula VI is a mixed anhydride. Mixed anhydrides can be formed from the carboxylic acid intermediate by a wide variety of methods using such reagents as alkyl chlorocarbonates, preferably methyl chlorocarbonate or isobutyl chlorocarbonate, in a suitable organic solvent. The reaction can be performed in the presence of a suitable base or the carboxylic acid can first be converted to a salt. Suitable bases are chemical compounds that are sufficiently basic to prevent the reaction medium from becoming acidic but which do not themselves form significant quantities of by-products by reaction with other chemical regents, intermediates, or reaction products. Examples of suitable bases include tertiary amines, such as triethylamine, tributylamine, and N-methylmorpholine; hindered secondary amines, such as 2,2,6,6-tetramethylpiperidine; nitrogen-containing heteroaromatic species, such as pyridine, quinoline, and dimethylaminopyridine. A preferred base is a tertiary amine such as tributylamine. If salt formation is used instead, the carboxylic acid can be allowed to react with a base that does not release water or an alcohol as a by-product. Suitable bases for salt formation include alkali metal carbonates, such as lithium, sodium, and potassium carbonates; alkali metal hydrides, such as sodium and potassium hydrides; alkali metal salts of amines, such as lithium diisopropylamide and lithium hexamethyldisilazide; and other strong bases known in the art. A preferred base is n-butyllithium. By whichever means the mixed anhydride is formed, the organic solvent must be compatible with the basic conditions used. Suitable organic solvents include alkanes and cycloalkanes; ethers and cyclic ethers, such as diethyl ether, tetrahydrofuran, tetrahydropyran, and dioxane; aromatic hydrocarbons, such as dimethylforamide and N,N-dimethylacetamide; N-substituted lactams, such as N-methylpyrrolidinone and N-methylpiperidinone; cyanoalkanes, such as acetonitrile and propanenitrile; and other organic solvents known in the art. A preferred organic solvent is tetrahydrofuran.

Scheme B illustrates the preparation of alcohols of this invention of Formula IX (that is, Formula I wherein $R^2$ is hydrogen) and of derivatized alcohols of this invention of Formula X (that is, Formula I wherein $R^2$ is a group other than hydrogen).

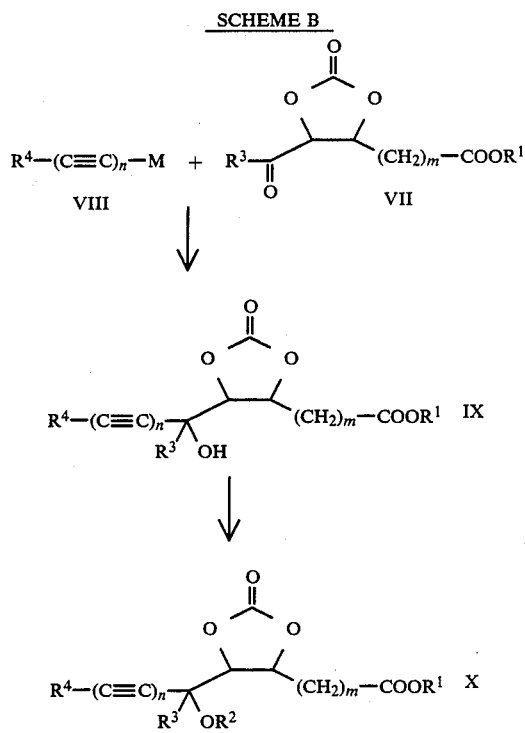

Aldehydes or ketones of Formula VII (that is, Formula VI wherein W is $R^3$) react with metallated acetylenes of Formula VIII, wherein M is a suitable metal or metal-containing species, to form alcohols of this invention of Formula IX. Metallated acetylenes are prepared from corresponding acetylenes using methods known in the art, with the metal or metal-containing species M selected so as to allow the metallated acetylenes to react with the carbonyl group attached to $R^3$ without reacting significantly with other functionalities within compounds of Formula VII. Suitable metals include alkali metals (preferably lithium) and alkaline earth metals (preferably magnesium). A preferred metallated acetylene species is a lithium acetylide formed in situ by the reaction of methyllithium with a silylated acetylene precursor of the formula

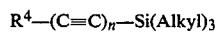

$$R^4-(C{\equiv}C)_n-Si(Alkyl)_3$$

in a suitable organic solvent. The metallated acetylene thus formed is then allowed to react with an aldehyde or ketone of Formula VII to form an alcohol of Formula IX. The silylated acetylene precursors are readily prepared by exposing metallated acetylenes (derived from terminally unsubstituted acetylenes) to trialkyl-silylhalides, a method of particular use for compounds in which $R^4$ is itself a trialkylsilyl group. Suitable organic solvents are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is an ether or cyclic ether such as diethyl ether or tetrahydrofuran.

Conversion of alcohols of Formula IX to derivatized alcohols of Formula X is effected by methods known in the art. For example, alkyl and aralkyl ethers can be formed by any of several alkylation methods known in the art. Silylated derivatives can be formed by reaction of the alcohol group with various silylating reagents, such as trialkylsilyl halides or hexaalkylsilazines, using methods well known in the art. Acylated derivatives can be formed by reaction with O-acylating reagents, such as acyl halides, acyl anhydrides, or isocyanates, using methods well known in the art.

Scheme C illustrates the preparation of ketones of this invention of Formula XII (that is, Formula I wherein $R^2$ an $R^3$ together are a bond). Scheme C also illustrates an alternative method for preparing alcohols of this invention of Formula XIII (that is, Formula I wherein $R^2$ and $R^3$ are both hydrogen).

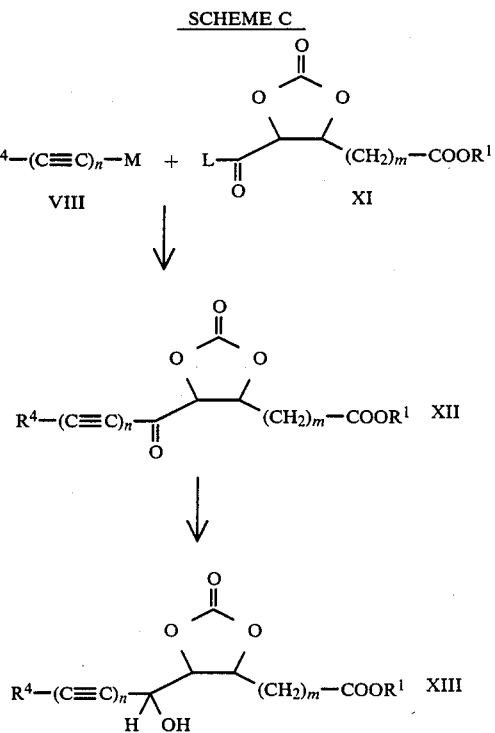

Activated acyl compounds of Formula XI (that is, Formula VI wherein W is a leaving group L) react with metallated acetylenes of Formula VIII, wherein M is a suitable metal or metal-containing species, to form ketones of this invention of Formula XII. Metallated acetylenes are prepared from corresponding acetylenes using methods known in the art, with the metal or metal-containing species M selected so as to allow the metallated acetylenes to react with the activated acyl group without reacting significantly with other functionalities within compounds of Formula XI. For acyl halides of Formula XI (that is, wherein L is a halogen, preferably chlorine or bromine), preferred metals include transition metals, such as copper, and transition metal complexes, preferably copper-lithium combinations that can be preformed or prepared in situ. For mixed anhydrides of Formula XI (that is, wherein L is O-acyl), the preferred metallated acetylene species is an organolithium compound of the formula

complexed with a Lewis acid (preferably boron trifluoride) in a suitable organic solvent. The metallated acetylene thus formed is then allowed to react with an activated acyl compound of Formula XI to form a ketone of Formula XII. Suitable organic solvents are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is an ether or cyclic ether such as diethyl ether or tetrahydrofuran.

Conversion of ketones of Formula XII to alcohols of Formula XIII can be effected using reduction methods well known in the art. For example, reduction can be effected using catalytic reduction or reaction with hydride reducing reagents such as modified alkali-metal aluminum hydrides or borohydrides. The alcohols XIII thus prepared can be derivatized using methods described above for Scheme B.

The preferred embodiments of this invention include compounds of the following general formula

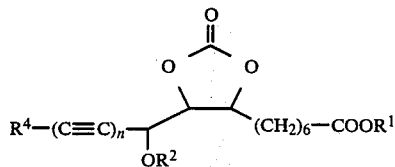

wherein $R^1$ is $C_1$-$C_6$ alkyl, preferably methyl; $R^2$ is hydrogen or $C_1$-$C_6$ alkyl; $R^4$ is $C_1$-$C_6$ alkyl or tris(-$C_1$-$C_6$ alkyl)silyl, preferably methyl or trimethylsilyl; and n is 2 or 3.

The compounds of this invention are useful in the treatment of fungal diseases and hypercholesterolemic conditions. Antifungal activity is illustrated using an assay against a Candida albicans strain. Antihypercholesterolemic activity is illustrated by inhibition of acetoacetyl-coenzyme A thiolase, the enzyme involved in an early stage of cholesterol biosynthesis.

Antifungal Assay

Antifungal activity was determined against Candida albicans MY 1055, a yeast strain maintained by Merck and Co., Rahway, New Jersey. Minimum inhibitory concentrations were determined using a starting inoculum of $3-5\times10^{-4}$ CFU/ml. The medium was Yeast Nitrogen Base/0.5% glucose. Test compounds were dissolved in a minimum amount of 50% aqueous ethanol and diluted to final concentrations with yeast medium. Samples were incubated at 37° C. for 18 hours. The minimum inhibitory concentration (MIC), reported in μg/ml, is the lowest concentration of test compound that inhibits visible growth. The MIC's for representative compounds of this invention are listed in Table I.

TABLE I

| Activity against Candida albicans MY 1055 | |
|---|---|
| Compound (Example No.) | MIC (μg/ml) |
| Ex. 5 | 0.078 |
| Ex. 6 | 0.6 |
| Ex. 13 | 5 |

Acetoacetyl-Coenzyme A Thiolase Inhibition

Acetoacetyl-coenzyme A thiolase was prepared from the livers of Sprague Dawley rats treated in the diet for one week with 0.075% lovastatin to induce the enzyme. Acetoacetyl-coenzyme A thiolase was purified through the DEAE-cellulose step essentially as described by Mehrabian et al., J. Biol. Chem., 261, 16249-16255 (1986), but modified slightly by carrying out the 30-50% ammonium sulfate precipitation of the enzyme and a dialysis before the DEAE-cellulose step. The 0.06M eluate described by Mehrabian et al. contained the acetoacetyl-coenzyme A thiolase. The isolate was concentrated by ammonium sulfate precipitation, dissolved in the buffer used for elution, and stored at $-70°$ C.

Inhibition of acetoacetyl-coenzyme A thiolase was measured by coupling the formation of acetoacetyl-coenzyme A to its subsequent reduction by β-hydroxybutyryl-coenzyme A dehydrogenase to β-hydroxybutyryl-coenzyme A and monitoring the resultant oxidation of NADH with a spectrophotometer set at 340 nm. Mixtures of 0.016 units of β-hydroxybutyryl-coenzyme A dehydrogenase, 16.2 μg of acetoacetyl-coenzyme A thiolase, and test quantities of the test compounds dissolved in dimethyl sulfoxide and water (sufficient to bring to final volume) were incubated with 71.4 mM Tris-HCl (pH 7.5), 0.71 mM EDTA, 10.7 mM magnesium chloride, 0.53 mM dithiothreitol, 0.21 mM NADH (total volume of 0.140 ml) until a stable base line was obtained. Reaction was initiated by addition of 10 μl of acetoacetyl-coenzyme A, giving a concentration of 2.85 mM. Reaction was measured at room temperature for a time period necessary to produce a measurable reaction rate. An $IC_{50}$, the concentration that inhibits 50% of the acetoacetyl-coenzyme A thiolase activity, was determined for each test compound. The $IC_{50}$'s for representative compounds of this invention are listed in Table II. The $IC_{50}$ of 5-(1-hydroxy-2,4,6-heptatriynyl)-2-oxo-1,3-dioxolane-4-heptanoic acid has been reported as $1\times10^{-8}$M. See U.S. patent application Ser. No. 07/053,973, filed May 26, 1987.

TABLE II

| Inhibition of Acetoacetyl-coenzyme A thiolase | |
|---|---|
| Compound (Example No.) | MIC (μM) |
| Ex. 5 | 0.062 |
| Ex. 6 | 0.99 |
| Ex. 13 | 0.56 |

By virtue of their antifungal and antihypercholesterolemic activities, the compounds of Formula I are useful in treating fungal diseases and hypercholesterolemia in mammals. A physician or veterinarian of ordinary skill can readily determine whether a subject exhibits the conditions. Regardless of the route of administration selected, the compounds of the present invention can be formulated into pharmaceutically acceptable dosage forms by conventional methods known to those skilled in the art. The non-ester compounds of this invention may also be formulated as pharmaceutically acceptable base addition salts. Moreover, the compounds or their salts may be used in a suitable hydrated form.

The compounds of this invention may be used in any of a variety of pharmaceutical preparations. The compounds can be administered orally in such oral dosage forms as tablets, capsules, pills, powders, granules, elixirs, or syrups. The compounds may be administered by injection intravascularly, intraperitioneally, subcutaneously, or intramuscularly using forms known to the pharmaceutical art. The compounds may also be administered topically using forms known to the pharmaceutical art. In general, the preferred form of administration is by injection.

For the orally administered pharmaceutical compositions and methods of the present invention, a therapeutically effective amount of the foregoing active ingredients will typically be administered in admixture with suitable pharmaceutical diluents, excipients, or carriers (collectively referred to herein as "carrier" materials) suitably selected with respect to the intended form of administration (that is, oral tablets, capsules, pills, powders, granules, elixirs, syrups, and the like) and consistent with conventional pharmaceutical practice. For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, and combinations thereof. Lubricants for use in these dosage forms include boric acid, sodium benzoate, sodium acetate, sodium chloride, and the like, or combinations thereof. Disintegrators include without limitation starch, methylcellulose, agar, bentonite, guar gum, and the like, or combinations thereof. Sweetening agents and preservatives can also be included where appropriate.

For the injectable pharmaceutical compositions and methods of the present invention, a therapeutically effective amount of the foregoing active ingredients will typically be administered in such forms as solutions, suspensions, or emulsions in oily or aqueous carriers. Suitable carriers include water, saline, aqueous dextrose, polyethylene glycol, various buffers, and the like. The infectable pharmaceutical compositions may include various formulatory agents known in the art. The injectable pharmaceutical compositions may be prepared in unit dosage form or in multidose containers or may be prepared in powdered form for reconstitution at the time of delivery with a suitable carrier, such as sterile water.

For the topically applied pharmaceutical compositions of the present invention, a therapeutically effective amount of the foregoing active ingredients will typically be formulated in hydrophobic or hydropphilic bases as ointments, creams, lotions, paints, or powders.

By whatever route of administration selected, a therapeutically effective but non-toxic amount of the compound is employed in treatment. The dosage regimen for preventing or treating fungal diseases or hypercholesterolemic conditions with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until an optimal response is obtained. Doses for injection are ordinarily in the range of about 1 mg/kg up to about 50 mg/kg, preferably in the range of about 10 mg/kg.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsuis unless otherwise noted.

DESCRIPTION OF THE PREFERRED EMBODIMENTS

EXAMPLE 1

8-Hydroxy-9-decenoic acid, methyl ester

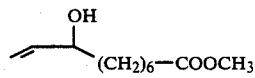

Methyl 8-oxooctanoate (76.1 mg, 442 μmols) was dissolved in dry tetrahydrofuran (THF)(2.0 ml) and cooled to −78° C. A solution of vinyl magnesium bromide in THF (442 μl, 442 μmol) was added dropwise over ten minutes. The solution was stirred at −78° C. for thirty minutes and then allowed to warm to ambient temperature whereupon saturated aqueous NH$_4$Cl (0.6 ml) was added all at once. The resulting mixture was partitioned between diethyl ether and water and the aqueous phase extracted once with diethyl ether. The resulting combined ether phases were washed with brine, dried with MgSO$_4$, filtered, and concentrated to a crude oil (82.6 mg). The crude oil was purified via preparative layer chromatography eluting with 5% Et$_2$O:CH$_2$Cl$_2$ to yield the title compound (59.9 mg, 68%). Structure assignment was supported by nmr spectroscopy.

$^1$H NMR (300 MHz, CDCl$_3$): δ (ppm) 2.097 (1H, s); 2.302, (2H, t, J=7.8 Hz); 3.663 (3H, s); 4.091 (1H, qt, J=6.5, 1.9 Hz); 5.100 (1H, dt, J=10.4, 1.9 Hz); 5.219 (1H, dt, J=16.9, 1.9 Hz); 5.859 (1H, ddd, J=16.7, 10.6, 6.1 Hz).

EXAMPLE 2

8(S)-Hydroxydecanoic acid, 9(R),10-epoxide, methyl ester

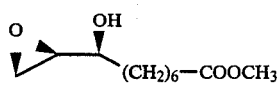

Molecular sieves (2.14 g powdered 3 A) were placed in a flask containing CH$_2$Cl$_2$ (35 ml) stirred at ambient temperature under an inert atmosphere. To this mixture was added Ti(OiPr)$_4$ (747 μl, 2.504 mmol) via syringe and the resulting solution was cooled to −20° C. (+)-Diisopropyl tartrate (632 μl, 3.005 mmol) was added next, immediately followed by 8-hydroxy-9-decenoic acid methyl ester (500 μl, 2.504 mmol; see Example 1). After stirring this mixture an additional 20 minutes at −20° C., a 3M solution of t-butyl hydroperoxide (500.8 μl, 1.502 mmol) in 2,2,4-trimethylpentane was added dropwise. The cooling bath was removed and the reaction was allowed to stir overnight at ambient temperature. The reaction was quenched with an aqueous solution of FeSO$_4$·7H$_2$O (835 mg, 3.005 mmol) and tartaric acid (227 mg, 1.502 mmol) in water (2.5 ml). After stirring for an additional 15 minutes, the mixture was decanted and filtered through a filtering aid. The filtering aid was washed well with water and diethyl ether. The filtrate layers were separated and the organic phase washed three times with water. The combined aqueous phases were extracted twice with diethyl ether. The ether layers were combined and washed once with brine, dried with MgSO$_4$, filtered, and concentrated to a clear oil (1.2846 g).

Purification via medium pressure column chromatography on silica gel (eluting with 1:1 ethyl acetate:hexanes) afforded the title compound as a clear oil (194.6 mg, 36%, 72% of theoretical). Structure assignment was supported by nmr spectroscopy. Optical rotation was determined in dichloromethane.

$^1$H NMR (300 MHz, CDCl$_3$): δ (ppm) 1.817 (1H, s); 2.312 (2H, t, J=7.9 Hz); 2.736 (1H, t, J=4.8 Hz); 2.812 (1H, dd, J=2.7, 6.0 Hz); 3.017 (1H, q, J=3.6 Hz); 3.670 (3H, s); 3.836 (1H, q, J=3.9 Hz). α$_{[D]}$ (c 1.82, CH$_2$Cl$_2$)=+10.5°.

EXAMPLE 3

8(S)-Phenylaminocarbonyloxydecanoic acid, 9(R),10-epoxide, methyl ester

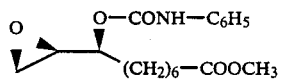

8(S)-Hydroxydecanoic acid, 9(R),10-epoxide methyl ester (63.7 mg, 294.2 μmol; see Example 2) and phenyl isocyanate (35.2 μl, 323.6 μmol) were stirred in acetonitrile (1.5 ml) for 1 week at ambient temperature. The resulting solution was evaporated to dryness, dissolved in CH$_2$Cl$_2$, and filtered. The filtrate was purified by silica gel preparative layer chromatography (eluting with 10% diethyl ether:CH$_2$Cl$_2$) to furnish the title compound as a clear oil (65.3 mg, 66%). Structure assignment was supported by nmr spectroscopy. Optical rotation was determined in dichloromethane.

$^1$H NMR (300 MHz, CDCl$_3$): δ (ppm) 2.308 (2H, tJ=7.4 Hz); 2.793 (2H, d, J=3.4 Hz); 3.012 (1H, dt, J=5.0, 3.2 Hz); 3.664 (3H, s); 4.685 (1H, q, J=6.3 Hz); 6.712 (1H, bs); 7.067 (1H, t, J=7.1 Hz). α$_{[D]}$ (c 1.04, CH$_2$Cl$_2$)=+11.1°.

EXAMPLE 4

Methyl 8,9,10-trihydroxydecanaoate-8,9-carbonate

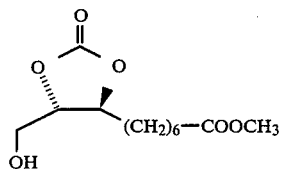

8(S)-Phenylaminocarbonyloxydecanoic acid, 9(R),10-epoxide, methyl ester (61.0 mg, 182 μmol; see Example 3) was dissolved in diethyl ether (4.0 ml) and cooled to −20° C. To this solution was added boron trifuoride etherate (24.4 μl, 198 μmol) dropwise. A white precipitate developed almost immediately. After stirring for 75 minutes, 1N sulfuric acid (2.0 ml) was added and the cooling bath removed. After stirring an additional hour, the mixture was diluted with diethyl ether. The ether was washed twice with water, dried once with brine, dried with MgSO$_4$, filtered, and concentrated to a clear oil (39.4 mg). The crude product was purified by silica gel preparative layer chromatography (eluting twice with 1:1 ethyl acetate:hexanes) to afford the title compound (32.8 mg, 69%). Structure assignment was supported by nmr and infrared spectroscopy.

$^1$H NMR (300 MHz, CDCl$_3$): δ (ppm) 2.133 (1H, t, J=6.3 Hz); 2.315 (2H, t, J=7.4 Hz); 3.671 (3H, s); 3.696 (1H, ddd, J=3.3, 5.6, 10.8 Hz); 3.947 (1H, ddd, J=3.2, 5.4, 12.6 Hz); 4.327 (1H, dt, J=6.5, 3.3 Hz); 4.584 (1H, ddd, J=4.6, 6.0, 7.1 Hz). IR (CH$_2$Cl$_2$): 1803, 1730 cm$^{-1}$.

EXAMPLE 5

5-(1(S)-Hydroxy-7-(trimethylsilyl)-2,4,6-heptatriynyl)-2-oxo-4(S),5(S)-1,3-dioxolane-4-heptanoic acid, methyl ester

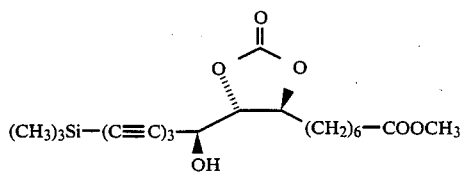

Dimethyl sulfoxide (27.2 μl, 384 μmols) was added via syringe to a solution of oxalyl chloride (31.3 μl, 358.4 μmols) in dry THF (2.0 ml) cooled to −60° C. under an inert atmosphere. The temperature of the cooling bath was allowed to gradually rise to −35° C., whereupon the mixture was stirred 5 minutes and then recooled to −60° C. A solution of methyl 8,9,10-trihydroxydecanoate-8,9-carbonate (66.7 mg, 256 μmols; see Example 4) in dry THF (1.5 ml) was added dropwise via syringe and the mixture warmed slowly to −35° C., at which point it was stirred an additional 15 minutes. Triethylamine (99.7 μl, 716.8 μmols) was added dropwise and the cooling bath removed. After slowly warming to and briefly stirring at ambient temperature, the mixture was recooled to −78° C., giving a crude 10-aldehyde mixture.

To bis-1,6-trimethylsilylhexa-1,3,5-triyne (83.9 mg, 384.1 μmols) stirring at −78° C. in dry THF (2.0 ml) under argon was added methyllithium in diethyl ether (274.3 μl, 384.1 μmols) and the mixture stirred 15 minutes. After being warmed to 0° C., the mixture was stirred for an additional one hour. The resultant 6-trimethylsilylhexa-1,3,5-triynyllithium reagent was added to the aldehyde mixture stirred at −78° C. The mixture was stirred for one hour at −78° C. and then quenched by dropwise addition of saturated ammonium chloride solution. The resulting heterogeneous mixture was warmed to ambient temperature and diluted with diethyl ether. After washing twice with pH 7 buffer, the ether layers were washed with brine, dried with MgSO4, and concentrated to a dark crude oil. The crude oil was purified by silica gel preparative layer chromatography on two 0.5 mm silica plates (eluting with two developments of 1:1 diethyl ether:hexane). After eluting the appropriate bands from the plates with hot THF, both the β C-10 hydroxy isomer (title compound) (Rf=0.48, 25.4 , mg, 24.5%) and the α isomer (Rf=0.37) were obtained in a combined yield of 39% in a ratio of 1:1.7 α:β. Structure assignment of the title compound was supported by nmr spectroscopy.

$^1$H NMR (300 MHz, CDCl$_3$): δ (ppm) 0.218 (9H, s); 2.329 (2H, t, J=7.4 Hz); 2.800 (1H, d, J=5.4 Hz); 3.679 (3H, s); 4.318 (1H, dd, J=3.3, 4.9 Hz); 4.74 (1H, dt, J=7.3, 5.1 Hz); 4.764 (1H, dd, J=4.4, 5.4 Hz).

EXAMPLE 6

5-(1R)-Hydroxy-7-(trimethylsilyl)-2,4,6-heptatriynyl)-2-oxo-4(S),5(S)-1,3-dioxolane-4-heptanoic acid, methyl ester

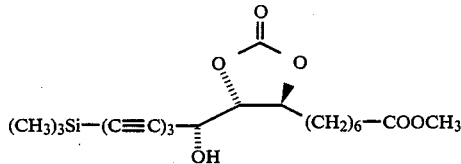

The title α C-10 hydroxy isomer (14.6 mg, 14.1%) of Example 5 was isolated from the slower eluting fractions of the chromatography described in Example 5. Structure assignment was supported by nmr spectroscopy.

$^1$H NMR (300 MHz, CDCl$_3$): δ (ppm) 0.218 (9H, s); 2.323 (2H, t, J=7.4 Hz); 2.614 (1H, d, J=5.4 Hz); 3.677 (3H, s); 4.318 (1H, t, J=5.0 Hz); 4.615 (1H, dt, J=7.2, 5.4 Hz); 4.640 (1H, dd, J=4.9, 5.3 Hz).

EXAMPLES 7–12

The compounds of Examples 7-12 were prepared according to the method of Example 5 using the appropriate lithiated diynyl and acetylenic precursors. Chromatographic separations produced both the β and α C-10 hydroxy isomers. Structure assignments were supported by nmr spectroscopy.

EXAMPLE 7

5-(1(S)-Hydroxy-5-(trimethylsilyl)-2,4-pentadiynyl)-2-oxo-4(S),5(S)-1,3-dioxolane-4-heptanoic acid, methyl ester

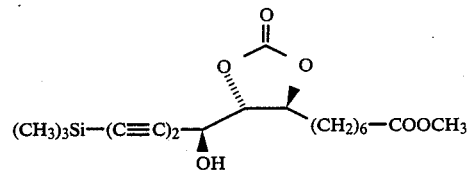

$^1$H NMR (300 MHz, CDCl$_3$): δ (ppm) 0.214 (9H, s); 2.323 (2H, t, J=7.5 Hz); 2.417 (1H, d, J=5.4 Hz); 3.676 (3H, s); 4.304 (1H, dd, J=3.3, 4.9 Hz); 4.727 (2H, m).

EXAMPLE 8

5-(1(R)-Hydroxy-5-(trimethylsilyl)-2,4-pentadiynyl)-2-oxo-4(S),5(S)-1,3-dioxolane-4-heptanoic acid, methyl ester

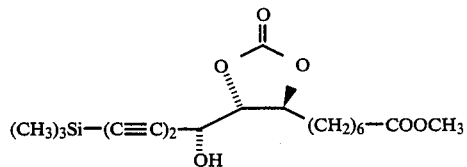

$^1$H NMR (300 MHz, CDCl$_3$): δ (ppm) 0.212 (9H, s); 2.318 (2H, t, J=7.4 Hz); 2.479 (1H, d, J=5.1 Hz); 3.676 (3H, s); 4.302 (1H, t, J=5.1 Hz); 4.628 (2H, m).

EXAMPLE 9

5-(1(R)-Hydroxy-3-(trimethylsilyl)-2-propynyl)-2-oxo-4(S),5(S)-1,3-dioxolane-4-heptanoic acid, methyl ester

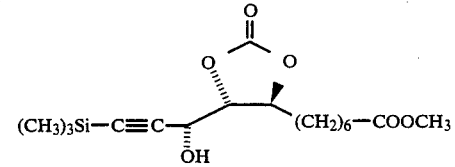

$^1$H NMR (300 MHz, CDCl$_3$): δ (ppm) 0.190 (9H, s); 2.262 (1H, d, J=4.9 Hz); 2.314 (2H, t, J=7.4 Hz); 3.673 (3H, s); 4.287 (1H, t, J=5.3 Hz); 4.548 (1H, t, J=5.1 Hz); 4.618 (1H, dt, J=7.2, 5.4 Hz).

EXAMPLE 10

5-(1(R)-Hydroxy-3-(trimethylsilyl)-2-propynyl-2-oxo-4(S),5(S)-1,3-dioxolane-4-heptanoic acid, methyl ester

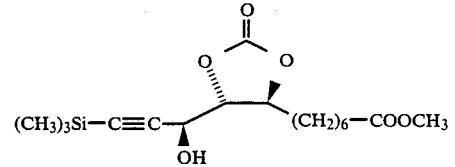

$^1$H NMR (300 MHz, CDCl$_3$): δ (ppm) 0.185 (9H, s); 2.285 (1H, d, J=3.8 Hz); 2.315 (2H, t, J=7.2 Hz); 3.672 (3H, s); 4.310 (1H, dd, J=3.0, 5.0 Hz); 4.651 (1H, dd, J=3.2, 5.3 Hz); 4.727 (1H, q, J=6.0 Hz).

EXAMPLE 11

5(1(S)-Hydroxy-2,4-hexadiynyl-2-oxo-4(S),5(S)-1,3-dioxolane-4-heptanoic acid, methyl ester

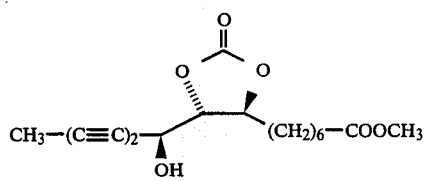

$^1$H NMR (300 MHz, CDCl$_3$): δ 1.964 (ppm) (3H, s); 2.322 (2H, t, J=7.4 Hz); 2.457 (1H, d, J=4.3 Hz); 3.677 (3H, s); 4.302 (1H, dd, J=3.2, 4.9 Hz); 4.726 (2H, m).

EXAMPLE 12

5-(1(R)-Hydroxy-2,4-hexadiynyl-2-oxo-4(S),5(S)-1,3-dioxolane-4-heptanoic acid, methyl ester

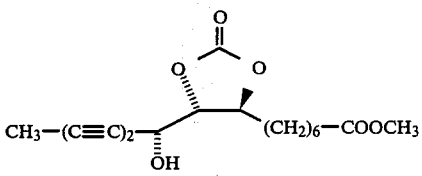

$^1$H NMR (300 MHz, CDCl$_3$): δ (ppm) 1.958 (3H, s); 2.317 (2H, t, J=7.4 Hz); 2.379 (1H, d, J=5.1 Hz); 3.674 (3H, s); 4.292 (1H, t, J=5.2 Hz); 4.605 (2H, m).

EXAMPLE 13

5-(1(R)-Methoxy-2,4,6-octatriynyl)-2-oxo-4(S),5(S)-1,3-dioxolane-4-heptanoic acid, methyl ester

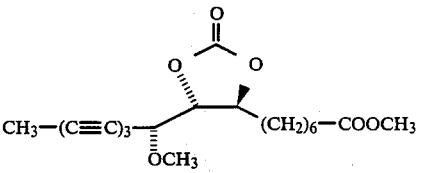

A 4.2 mg/ml solution in CH$_2$Cl$_2$ of 5-(1(R)-hydroxy-2,4,6-octatriynyl)-2-oxo-4(S),5(S)-1,3-dioxolane-4-heptanoic acid (60 ml, 0.792 mmols; see, for example, Lewis and Menes, Tetrahedron Lett., 28, 5129–5132 (1987)) was evaporated down three times with ethyl acetate until a volume of 12 ml was obtained. Silver oxide (1.8 g, freshly prepared) was added to this solution in the dark and the flask covered with aluminum foil to exclude light. Methyl iodide (1.5 ml) was added and the mixture heated at 50° C. overnight with stirring. The liquid was then decanted and applied directly to a silica gel column, whereupon it was eluted first with 30% ethyl acetate:hexanes (1 liter) followed by 50% ethyl acetate:hexanes (1 liter). The fractions containing the desired compound were combined and dried in vacuo for 1.5 hours. Repurification three times by preparative layer chromatography (eluting with 30% ethyl acetate:hexanes) afforded the pure title compound (32.9 mg, 11%) as a light brown oil. Structure assignment was supported by nmr spectroscopy.

$^1$H NMR (300 MHz, CDCl$_3$): δ (ppm) 1.992 (3H, s); 2.314 (2H, d, J=7.4 Hz); 3.463 (3H, s); 3.674 (3H, s); 4.296 (2H, m); 4.599 (1H, q, J=5.6 Hz).

EXAMPLE 14

5-(1-Oxo-2-heptynyl)-2-oxo-4(S),5(S)-1,3-dioxolane-4-heptanoic acid, methyl ester

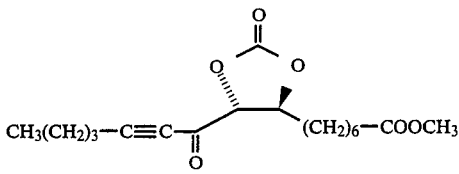

Methyl 8,9,10-trihydroxydecanoate-8,9-carbonate (503 mg, 1.93 mmols; see Example 4) was dissolved in acetone (20 ml) and Jones reagent (3.2 ml) was added dropwise. The resulting orange mixture was stirred for two hours at room temperature, at which time a green precipitate had developed. After dilution with diethyl ether (50 ml) and water (25 ml), the layers were separated. The ether layer was washed four times with water and the combined aqueous layers extracted four times with diethyl ether. The combined organic phases were dried with MgSO$_4$, filtered and concentrated in vacuo to afford the 10-carboxylic acid (503.3 mg, 95%). The carboxylic acid (18 mg, 65.6 μmols) was dissolved in dry THF (1.0 ml) at ambient temperature under an inert atmosphere. A solution of n-butyllithium in hexane (24.2 μl, 65.6 μmols) was added dropwise, followed by addition of methyl chloroformate (100 μl, 1.294 mmols). After stirring at ambient temperature for thirty minutes, the solution was evaporated under reduced pressure and the resulting mixed anhydride dried in vacuo for two hours. The residue was dissolved in diethyl ether, filtered, and dried in vacuo overnight.

To hexyne (6.4 μl, 55.6 mmols) dissolved in dry THF (1.0 ml) stirring at 0° C. under an inert atmosphere was added n-butyllithium (18.7 μl, 50.6 μmols) in hexane. After stirring for five minutes, the reaction mixture was cooled to −78° C. Boron trifluoride etherate (6.2 μl, 50.6 μmols) was added dropwise and stirring continued for 15 minutes. The mixed anhydride prepared above was dissolved in dry THF (1.0 ml) and added dropwise over a five minute period. After stirring for 1.5 hours at −78° C., the reaction mixture was allowed to warm to ambient temperature and then quenched by addition of 5 drops of saturated ammonium chloride. The mixture was diluted with diethyl ether and washed twice with water and once with brine, dried with MgSO$_4$, filtered, and concentrated under reduced pressure to the crude oily title ketone (16.5 mg). Purification by preparative layer chromatography on silica gel (eluting with 5% diethyl ether:CH$_2$Cl$_2$), afforded the pure title compound (1.5 mg, 6.3% overall) as a clear film. Structure assignment was supported by nmr spectroscopy.

$^1$H NMR (300 MHz, CDCl$_3$): δ 0.941 (3H, t, 7.3 Hz); 2.314 (2H, t, J=7.4 Hz); 2.473 (2H, t, J=7.0 Hz); 3.674 (3H, s); 4.542 (1H, d, J=Hz); 4.610 (1H, q, J=6.9 Hz).

EXAMPLE 15

5-(1(S)-Hydroxy-2-heptynyl)-2-oxo-4(S),5(S)-1,3-dioxolane-4-heptanoic acid, methyl ester

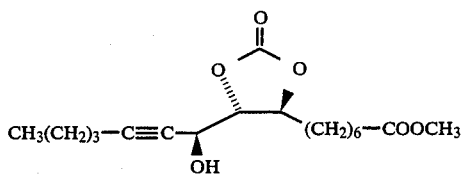

To 5-(1-oxo-2-heptynyl)-2-oxo-4(S),5(S)-1,3-dioxolane-4-heptanoic acid methyl ester (12.8 mg, 37.8 mmols) stirring in methanol at ambient temperature was added sodium borohydride. After 20 minutes, the reaction was quenched by addition of three drops of acetic acid. The mixture was partitioned between diethyl ether and 1N hydrochloric acid. The ether layer was washed once with brine, dried with MgSO$_4$, filtered, and concentrated to a crude semisolid residue (20.8 mg). Purification by preparative layer chromatography on silica gel (eluting twice with 2:1 diethyl ether:hexanes) afforded the pure title compound (3.8 mg) as a clear oil. Structure assignment was supported by nmr spectroscopy.

$^1$H NMR (300 MHz, CDCl$_3$): δ (ppm) 0.941 (3H, t, 7.1 Hz); 2.225 (2H, dt, J=2.5, 6.2 Hz); 2.314 (2H, t, J=7.4 Hz); 3.671 (3H, s); 4.239 (1H, dd, J=2.8, 5.2 Hz); 4.616 (1 h, m); 4.653 (1H, dt, J=7.5, 5.2 Hz).

EXAMPLE 16

5-(1(R)-Hydroxy-2-heptynyl)-2-oxo-4(S),5(S)-1,3-dioxolane-4-heptanoic acid, methyl ester

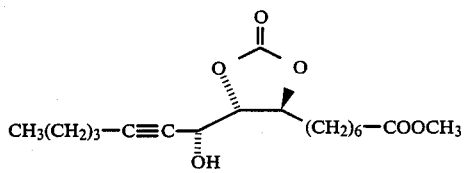

Other eluate fractions from the chromatography described in Example 15 furnished the title compound (2.0 mg) as a clear oil. Structure assignment was supported by nmr spectroscopy.

$^1$H NMR (300 MHz, CDCl$_3$): δ (ppm) 0.941 (3H, t, 7.1 Hz); 2.166 (1H, d, J=4.2 Hz); 2.233 (2H, dt, J=2.5, 6.2 Hz); 2.313 (2H, t, J=7.4 Hz); 3.671 (3H, s); 4.261 (1H, t, J=5.3 Hz); 4.551 (1H, tt, J=2.6, 5.3 Hz); 4.618 (1H, dt, J=7.0, 5.3 Hz).

What is claimed is:

1. A compound of the formula:

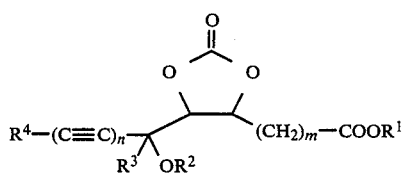

wherein
R$^1$ is:
 (a) hydrogen;
 (b) C$_1$–C$_6$ alkyl;
 (c) C$_7$–C$_{14}$ aralkyl;
 (d) tris(C$_1$–C$_6$ alkyl)silyl; or
 (e) a pharmaceutically acceptable cation;
R$^2$ is:
 (a) hydrogen;
 (b) C$_1$–C$_6$ alkyl;
 (c) C$_7$–C$_{14}$ aralkyl;
 (d) tris(C$_1$–C$_6$ alkyl)silyl;
 (e) C$_2$–C$_6$ alkanoyl;
 (f) C$_2$–C$_7$ alkoxycarbonyl; or
 (g)

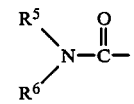

wherein R$^5$ and R$^6$ are independently:
 (i) hydrogen;
 (ii) C$_1$–C$_6$ alkyl; or
 (iii) phenyl;
R$^3$ is:
 (a) hydrogen; or
 (b) C$_1$–C$_6$ alkyl;
R$^4$ is:
 (a) C$_1$–C$_6$ alkyl;
 (b) C$_7$–C$_{14}$ aralkyl; or
 (c) tris(C$_1$–C$_6$ alkyl)silyl;
m is an integer of from about 2 to 8; and
n is an integer of from about 1 to 4.

2. A compound according to claim 1 having the formula:

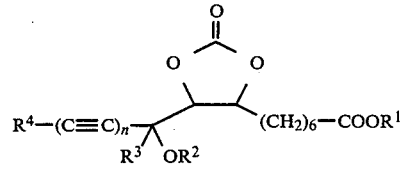

wherein
R$^1$ is:
 (a) hydrogen;
 (b) C$_1$–C$_6$ alkyl; or
 (c) a pharmaceutically acceptable cation;
R$^2$ is:
 (a) hydrogen;
 (b) C$_1$–C$_6$ alkyl;
 (c) C$_7$–C$_{14}$ alkyl;
 (d) tris(C$_1$–C$_6$ alkyl)silyl;
 (e) C$_2$–C$_6$ alkanoyl;
 (f) C$_2$–C$_7$ alkoxycarbonyl; or
 (g)

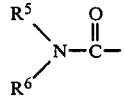

wherein
R$^5$ and R$^6$ are independently:
 (i) hydrogen;
 (ii) C$_1$–C$_6$ alkyl; or
 (iii) phenyl;
R$^3$ is hydrogen,
R$^4$ is:
 (a) C$_1$–C$_6$ alkyl;

(b) C₇–C₁₄ aralkyl; or
(c) tris(C₁–C₆ alkyl)silyl; and
n is an integer of from about 1 to 3.

3. A compound according to claim 2 having the formula:

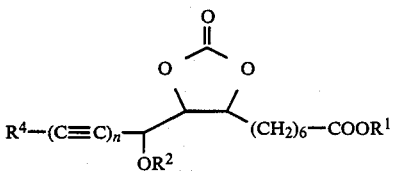

wherein
R¹ is:
(a) hydrogen;
(b) C₁–C₆ alkyl; or
(c) a pharmaceutical acceptable cation;
R² is:
(a) hydrogen;
(b) C₁–C₆ alkyl; or
(c) C₂–C₆ alkanoyl;
R⁴ is:
(a) C₁–C₆ alkyl; or
(b) tris(C₁–C₆ alkyl)silyl; and
n is an integer of from about 1 to 3.

4. A compound according to claim 3 wherein n is 3.
5. A compound according to claim 4 wherein R² is hydrogen.
6. A compound according to claim 5 which is 5-(1(R)-hydroxy-7-(trimethylsilyl)-2,4,6-heptatriynyl)-2-oxo-4(S),5(S)-1,3-dioxolane-4-heptanoic acid, methyl ester.
7. A compound according to claim 5 which is 5-(1(S)-hydroxy-7-(trimethylsilyl)-2,4,6-heptatriynyl)-2-oxo-4(S),5(S)-1,3-dioxolane-4-heptanoic acid, methyl ester.
8. A compound according to claim 4 wherein R² is C₁–C₆ alkyl.
9. A compound according to claim 5 which is 5-(1(R)-methoxy-2,4,6-octatriynyl)-2-oxo-4(S),5(S)-1,3-dioxolane-4-heptanoic acid, methyl ester.
10. A compound according to claim 3 wherein n is 2.
11. A compound according to claim 10 which is 5-(1(R)-hydroxy-5-(trimethylsilyl)-2,4-pentadiynyl)-2-oxo-4(S),5(S)-1,3-dioxolane-4-heptanoic acid, methyl ester.
12. A compound according to claim 10 which is 5-(1(S)-hydroxy-5-(trimethylsilyl)-2,4-pentadiynyl)-2-oxo-4(S),5(S)-1,3-dioxolane-4-heptanoic acid, methyl ester.
13. A compound according to claim 10 which is 5-(1(R)-hydroxy-2,4-hexadiynyl)-2-oxo-4(S),5(S)-1,3-dioxolane-4-heptanoic acid, methyl ester.
14. A compound according to claim 10 which is 5-(1(S)-hydroxy-2,4-hexadiynyl)-2-oxo-4(S),5(S)-1,3-dioxolane-4-heptanoic acid, methyl ester.
15. A compound according to claim 3 wherein n is 1.
16. A compound according to claim 15 which is 5-(1(R)-hydroxy-3-(trimethylsilyl)-2-propynyl)-2-oxo-4(S),5(S)-1,3-dioxolane-4-heptanoic acid, methyl ester.
17. A compound according to claim 15 which is 5-(1(S)-hydroxy-3-(trimethylsilyl)-2-propynyl)-2-oxo-4(S),5(S)-1,3-dioxolane-4-heptanoic acid, methyl ester.

18. A compound according to claim 15 which is 5-(1(R)-hydroxy-2-heptynyl)-2-oxo-4(S),5(S)-1,3-dioxolane-4-heptanoic acid, methyl ester.
19. A compound according to claim 15 which is 5-(1(S)-hydroxy-2-heptynyl)-2-oxo-4(S),5(S)-1,3-dioxolane-4-heptanoic acid, methyl ester.
20. A compound according to claim 2 having the formula:

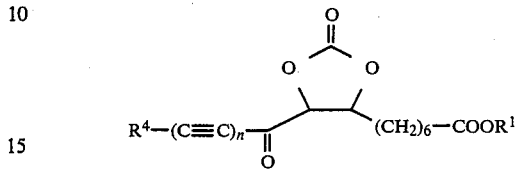

wherein
R¹ is:
(a) hydrogen;
(b) C₁–C₆ alkyl; or
(c) a pharmaceutically acceptable cation;
R⁴ is:
(a) C₁–C₆ alkyl; or
(b) tris(C₁–C₆ alkyl)silyl; and
n is an integer of from about 1 to 3.

21. A compound according to claim 20 which is 5-(1-oxo-2-heptynyl)-2-oxo-4(S),5(S)-1,3-dioxolane-4-heptanoic acid, methyl ester.
22. A pharmaceutical composition useful in the treatment of fungal diseases or hypercholesterolemic conditions comprising a therapeutically effective amount of at least one compound according to claim 1, together with one or more non-toxic pharmaceutically acceptable carriers.
23. A pharmaceutical composition according to claim 22 wherein said compound is selected from the group consisting of:
5-(1(R)-hydroxy-7-(trimethylsilyl)-2,4,6-heptatriynyl)-2-oxo-4(S),5(S)-1,3-dioxolane-4-heptanoic acid, methyl ester;
5-(1(S)-hydroxy-7-(trimethylsilyl)-2,4,6-heptatriynyl)-2-oxo-4(S),5(S)-1,3-dioxolane-4-heptanoic acid, methyl ester;
5-(1(R)-methoxy-2,4,6-octatriynyl)-2-oxo-4(S),5(S)-1,3-dioxolane-4-heptanoic acid, methyl ester;
5-(1(R)-hydroxy-5-(trimethylsilyl)-2,4-pentadiynyl)-2-oxo-4(S),5(S)-1,3-dioxolane-4-heptanoic acid, methyl ester;
5-(1(S)-hydroxy-5-(trimethylsilyl)-2,4-pentadiynyl)-2-oxo-4(S),5(S)-1,3-dioxolane-4-heptanoic acid, methyl ester;
5-(1(R)-hydroxy-2,4-hexadiynyl)-2-oxo-4(S),5(S)-1,3-dioxolane-4-heptanoic acid, methyl ester;
5-(1(S)-hydroxy-2,4-hexadiynyl)-2-oxo-4(S),5(S)-1,3-dioxolane-4-heptanoic acid, methyl ester;
5-(1(R)-hydroxy-3-(trimethylsilyl)-2-propynyl)-2-oxo-4(S),5(S)-1,3-dioxolane-4-heptanoic acid, methyl ester;
5-(1(S)-hydroxy-3-(trimethylsilyl)-2-propynyl)-2-oxo-4(S),5(S)-1,3-dioxolane-4-heptanoic acid, methyl ester;
5-(1(R)-hydroxy-2-heptynyl)-2-oxo-4(S),5(S)-1,3-dioxolane-4-heptanoic acid, methyl ester;
5-(1(S)-hydroxy-2-heptynyl)-2-oxo-4(S),5(S)-1,3-dioxolane-4-heptanoic acid, methyl ester; and
5(1-oxo-2-heptynyl)-2-oxo-4(S),5(S)-1,3-dioxolane-4-heptanoic acid, methyl ester.

* * * * *